United States Patent [19]

Fujiwara et al.

[11] 4,415,730
[45] Nov. 15, 1983

[54] 19-DEFORMYL-DEOXY-DESMYCOSIN

[75] Inventors: Tatsuro Fujiwara, Shizuoka; Eiichi Honda; Hideo Sakakibara, both of Mishima; Takao Hirano, Shizuoka, all of Japan

[73] Assignee: Toyo Jozo Kabushiki Kaisha, Shizuoka, Japan

[21] Appl. No.: 391,284

[22] Filed: Jun. 23, 1982

[30] Foreign Application Priority Data

Jun. 23, 1981 [JP] Japan ................................ 56-98105
Dec. 28, 1981 [JP] Japan ................................ 56-211648

[51] Int. Cl.³ ...................... A61K 31/71; C07H 17/08
[52] U.S. Cl. ...................................... 536/7.1; 424/180
[58] Field of Search ........................................ 536/7.1

[56] References Cited

U.S. PATENT DOCUMENTS 4,268,665  5/1981  Sakakibara et al. ................ 536/7.1
4,307,085  12/1981  Waitz et al. .......................... 536/7.1

Primary Examiner—Johnnie R. Brown
Assistant Examiner—Elli Peselev
Attorney, Agent, or Firm—Young & Thompson

[57] ABSTRACT

A compound of the formula

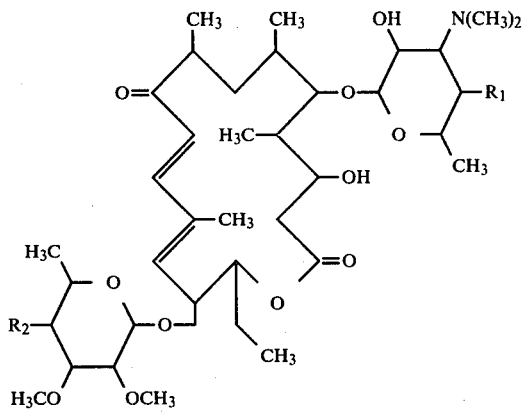

wherein $R_1$ and $R_2$ are hydrogen or hydroxyl and at least one of $R_1$ and $R_2$ is hydrogen, or a pharmaceutically acceptable salt thereof, has antibacterial activity against Gram positive bacteria and against macrolide-resistant A group bacteria.

4 Claims, No Drawings

19-DEFORMYL-DEOXY-DESMYCOSIN

This invention relates to novel derivatives of antibiotic tylosin. More particularly the present invention relates to compounds of the formula

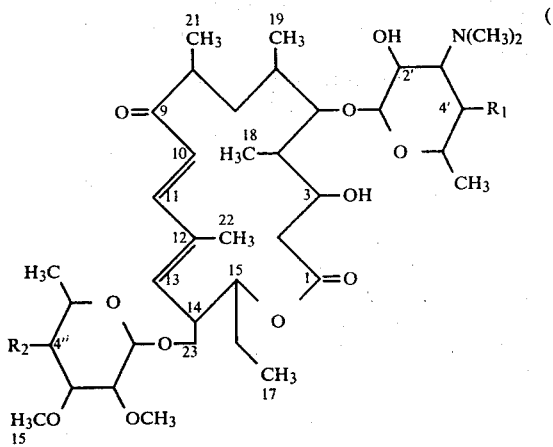

wherein $R_1$ and $R_2$ are hydrogen or hydroxyl and at least one of $R_1$ and $R_2$ is hydrogen, or a pharmaceutically acceptable salt thereof.

Examples of salt are salts of inorganic acids such as hydrochlorides, sulfates or phosphates and salts of organic acids such as acetates, propionates, tartrates, citrates, succinates, malates, aspartates or glutamates. Other non-toxic salts can be used.

The novel compound [1] has antibacterial activity against Gram positive bacteria which is equivalent to that of erythromycin, and has a stronger antibacterial activity against Gram positive bacteria than tylosin and desmycosin [4'-demycarosyl tylosin (Antibiotics and Chemotherapy, 11 (5), 328–334 (1961)]. The antibiotic compound [1] also has strong antibacterial activity against macrolide-resistant A group bacteria (clinical isolates that are resistant to erythromycin, oleandomycin and 16-member-ring macrolide antibiotics).

Compound [1] is stable in vivo, high in blood level and of quite low toxicity, and hence it may be useful for treatment for infectious diseases of humans and animals per oral administration, and also is useful for feed additives.

In the present specification, the product [1] and its intermediates are designated according to the position numbering given in formula [1].

A compound [1] of the present invention is produced by any of the following processes:

(A) A compound [1] wherein $R_1$ is hydrogen and $R_2$ is hydroxyl, i.e. 19-deformyl-4'-deoxy-desmycosin [1a]:

Compound [1a] can be prepared by deformylation of 4'-deoxy-desmycosin with $[(C_6H_5)_3P]_3RhCl$ in an inert organic solvent with heating.

The starting material 4'-deoxy-desmycosin can be obtained by the demycarosylation at position 4' of 2'-O-acetyltylosin with dilute acid, acetylating the 4''-hydroxyl group of the thus-obtained 2'-O-acetyl-desmycosin, trifluoromethanesulfonylating the 4'-hydroxyl group of the thus-obtained 2',4''-di-O-acetyl-desmycosin, iodinating at position 4' of the thus-prepared 2',4''-di-O-acetyl-4'-O-trifluoromethanesulfonyl-desmycosin, deacetylating at position 4'' of the thus-obtained 2',4''-di-O-acetyl-4'-deoxy-4'-iodo-desmycosin, then de-iodinating and deacetylating at position 2' of the thus-produced 2'-O-acetyl-4'-deoxy-4'-iodo-desmycosin. (Jap. Pat. Appln. No. 56-38375).

The above deformylation reaction proceeds usually with reflux of the reaction solvent. A preferred example of the inert organic solvent in the reaction is benzene. The reaction can be checked by thin layer chromatography (TLC) of silica gel, and is terminated upon the disappearance of 4'-deoxy-desmycosin.

Isolation of the product from the reaction mixture can be performed by extracting with dilute acid such as diluted hydrochloric acid, adjusting the extract with aqueous alkali such as aqueous ammonia to pH 9-10, extracting with a water-immiscible organic solvent such as chloroform, and distilling off the solvent.

Further purification can be performed by conventional isolation and purification procedures for macrolide antibiotics, for example adsorption chromatography using silica gel, active alumina and resin.

(B) A compound [1] wherein $R_1$ is hydroxy and $R_2$ is hydrogen, i.e. 19-deformyl-4''-deoxy-desmycosin [1b]:

Compound [1b] can be prepared by deformylating 4''-deoxy-desmycosin with $[(C_6H_5)_3P]_3RhCl$ in an inert organic solvent with heating.

The starting material 4''-deoxy-desmycosin can be prepared by diacetylating the 2',4'-hydroxyl group of desmycosin, trifluoromethanesulfonylating the 4''-hydroxyl group of the thus-obtained 2',4'-di-O-acetyl-desmycosin, halogenating at position 4'' of the thus-prepared 2',4'-di-O-acetyl-4''-O-trifluoromethanesulfonyl-desmycosin, dehalogenating at position 4'' of the thus-obtained 2',4'-di-O-acetyl-4''-deoxy-4''-halogeno-desmycosin, and de-diacetylating the thus-obtained 2',4'-di-O-acetyl-4''-deoxy-desmycosin. (Jap. Pat. Appln. No. 56-38375).

The deformylating reaction can be conducted in the same way as in the process (A).

Compound [1b] can also be produced by the following process:

The hydroxyl groups at positions 2' and 4' of 19-deformyl-desmycosin (Jap. Pat. Unexam. Publ. No. 56-55399) are diacetylated; the 4''-hydroxyl group of the thus-obtained 2',4'-di-O-acetyl-19-deformyl-desmycosin is trifluoromethanesulfonylated; the thus-obtained 2',4'-di-O-acetyl-4''-O-trifluoromethanesulfonyl-19-deformyl-desmycosin is halogenated at position 4''; the thus-prepared 2',4'-di-O-acetyl-19-deformyl-4''-halogeno-4''-deoxy-desmycosin is dehalogenated; and then the thus-prepared 2',4'-di-O-acetyl-19-deformyl-4''-deoxy-desmycosin is de-diacetylated.

Diacetylation is performed by reacting 19-deformyl-desmycosin with acetic anhydride in an inert organic solvent. The preferred inert organic solvents are, for example, dichloromethane, chloroform, dichloroethane and acetone. The reaction proceeds at room temperature and can be checked by silica gel TLC, and is terminated upon the disappearance of 19-deformyl-desmycosin. With the above acetylation reaction conditions, selective acetylation of the hydroxyl groups takes place at position 2' and 4'' in the four hydroxyl groups of 19-deformyl-desmycosin at positions 3, 2', 4' and 4''.

The trifluoromethanesulfonylation reaction can be conducted by reacting 2',4'-di-O-acetyl-19-deformyl-desmycosin with anhydrous trifluoromethanesulfonic acid $[(F_3CSO_2)_2O]$ in an inert organic solvent in the presence of a tertiary organic amine. The preferred inert organic solvents are dichloromethane, chloroform, dichloroethane or acetone. Examples of tertiary organic amines are pyridine, picoline, collidine, N-methylmorpholine, N-methylpiperidine and dimethylaniline. Pyridine is preferred. The reaction proceeds at lower temperature, e.g. below room temperature. The reaction progress can be checked by TLC and is terminated upon the disappearance of 2',4'-di-O-acetyl-19-deformyl-desmycosin.

The above 4"-halogenation is performed by reacting 2',4'-di-O-acetyl-4"-O-trifluoromethanesulfonyl-19-deformyl-desmycosin with alkali halide in an inert organic solvent. Preferred examples of inert organic acids are dimethoxyethane and acetone. Examples of alkali halides are alkali iodide, alkali bromide, alkali chloride and alkali fluoride. Most preferred are alkali iodides such as NaI, KI and LiI. The reaction can proceed with heating to below the boiling point of the mixture. The reaction progress can be checked by silica gel TLC and is terminated upon the disappearance of 2',4'-di-O-acetyl-4"-O-trifluoromethanesulfonyl-19-deformyl-desmycosin.

The dehalogenation at position 4" is performed by reacting 2',4'-di-O-acetyl-19-deformyl-4"-halogeno-4"-deoxy-desmycosin with tributyltin hydride and a catalytic amount of azobisisobutyronitrile in an inert organic solvent. The preferred inert organic solvents are benzene and toluene. The reaction usually proceeds with heating below the boiling point of the organic solvent in a stream of inert gas such as argon. The reaction progress can be checked by silica gel TLC and is terminated upon the disappearance of 2',4'-di-O-acetyl-19-deformyl-4"-halogeno-4"-deoxy-desmycosin.

The de-diacetylation can be performed by heating 2',4'-di-O-acetyl-19-deformyl-4"-deoxy-desmycosin in methanol. The reaction progress can be checked by silica gel TLC and is terminated upon observing the disappearance of 2',4'-di-O-acetyl-19-deformyl-4"-deoxy-desmycosin.

Isolation of an intermediate in the production of compound [1b], from the reaction mixture, can be effected by pouring the reaction mixture into water, adjusting to about pH 9 with an alkali such as aqueous ammonia, extracting with a water-immiscible organic solvent such as chloroform, washing and concentrating. Further purification can be effected by column chromatography using silica gel, active alumina or an adsorption resin.

Compound [1b] can be further purified by the same process, such as column chromatography.

(C) A compound [1] wherein $R_1$ and $R_2$ are both hydrogen, i.e. 4',4"-deoxy-19-deformyl-desmycosin [1c]:

The above compound [1c] can be produced by deformylating the 4',4"-dideoxy-desmycosin with $[(C_6H_5)_3P]_3RhCl$ in the presence of an inert organic solvent, with heating.

4',4"-dideoxy-desmycosin can be prepared by the demycarosylation at position 4' of 2'-O-acetyltylosin with dilute acid, acetylating the hydroxyl group at position 4" of the thus-obtained 2'-O-acetyl-desmycosin, trifluoromethanesulfonylating the hydroxyl group at position 4' of the thus-obtained 2',4"-di-O-acetyl-desmycosin, iodizing at position 4' the thus-prepared 2',4"-di-O-acetyl-4'-O-trifluoromethanesulfonyl-desmycosin, deacetylating at position 4" the thus-prepared 2',4"-di-O-acetyl-4'-deoxy-4'-iodo-desmycosin, trifluoromethanesulfonylating the hydroxyl group at position 4" of the thus-obtained 2'-O-acetyl-4'-deoxy-4'-iodo-desmycosin, iodizing at position 4" the thus-obtained 2'-O-acetyl-4'-deoxy-4'-iodo-4"-O-trifluoromethanesulfonyl-desmycosin, and deiodizing and deacetylating at position 2' the 2'-O-acetyl-4',4"-dideoxy-4',4"-diiodo-desmycosin.

Demycarosylation at position 4' can be performed by hydrolysis with dilute acid such as 0.3–0.5 N HCl. The reaction proceeds at room temperature and can be traced by TLC and is terminated upon the disappearance of 2'-acetyltylosin.

The above acetylation of the hydroxyl group at position 4" is performed by reacting with acetyl halide in an inert organic solvent in the presence of a tertiary organic amine. Examples of tertiary organic amines are pyridine, picoline, collidine, N-methyl-morpholine, N-methylpiperidine or dimethylaniline. Pyridine is preferred because it serves also as solvent. An example of an acetylhalide is acetylchloride. The reaction proceeds at room temperature and can be traced by silica gel TLC, then is terminated upon the disappearance of 2'-O-acetyl-desmycosin. Among the three hydroxyl groups at positions 3, 4' and 4" of 2'-O-acetyl-desmycosin, an acetyl group can be selectively introduced into the hydroxyl group at position 4" under the above acetylation conditions.

The above 4'-trifluoromethanesulfonylation is achieved by reacting 2',4"-di-O-acetyl-desmycosin with trifluoromethanesulfonyl-halide in an inert organic solvent in the presence of a tertiary organic amine. Examples of inert organic amines are dichloromethane, chloroform or dichloroethane. Examples of tertiary organic amines are pyridine, picoline, collidine, N-methylmorpholine, N-methylpiperidine, dimethylaniline, triethylamine or dimethylamino pyridine. Again, pyridine is preferred because it serves also as solvent. The trifluoromethanesulfonyl halide is ordinarily trifluoromethanesulfonylchloride ($CF_3SO_2Cl$). The reaction proceeds at a lower temperature than room temperature and can be traced by silica gel TLC, and is terminated upon the disappearance of 2',4"-di-O-acetyl-desmycosin.

The above 4'-iodization can be effected by reacting 2',4"-di-O-acetyl-4'-O-trifluoromethanesulfonyl-desmycosin with an alkali iodide in an inert organic solvent. The preferred organic solvent is hexamethylenephosphoramide (HMPA) or dimethylformamide. Examples of alkali iodides are NaI, KI or LiI. The reaction proceeds generally with heating, preferably at 50°–100° C. The reaction progress can be traced by silica gel TLC and is terminated upon the disappearance of 2',4"-di-O-acetyl-4'-O-trifluoromethanesulfonyl-desmycosin.

The above deacetylation at position 4" of 2',4"-di-O-acetyl-4'-deoxy-4'-iodo-desmycosin can be performed by treating with a dilute methanol solution of $NaOCH_3$. The concentration of the methanol solution of $NaOCH_3$ is approximately 0.05–0.3%. The reaction proceeds at room temperature, and can be traced by silica gel TLC, and is terminated upon observing the disappearance of 2',4"-di-O-acetyl-4'-deoxy-4'-iodo-desmycosin. The reaction can be stopped by adding water.

The 4"-trifluoromethanesulfonylation can be performed by reacting 2'-O-acetyl-4'-deoxy-4'-iododesmycosin with anhydrous trifluoromethanesulfonic acid $[(F_3CSO_2)_2O]$ in an inert organic solvent in the presence of a tertiary organic amine. The preferred inert organic solvents are dichloromethane, chloroform, dichloroethane or acetone. Examples of tertiary organic amines are pyridine, picoline, collidine, N-methylmorpholine, N-methylpiperidine and dimethylaniline; and again, pyridine is preferred. The reaction proceeds below room temperature. The reaction progress can be traced by silica gel TLC and is terminated upon the disappearance of 2'-O-acetyl-4'-deoxy-4'-iodo-desmycosin.

The 4''-iodization can be performed by reacting 2'-O-acetyl-4'-deoxy-4'-iodo-4''-O-trifluoromethanesulfonyl-desmycosin with an alkali iodide in an inert organic solvent. Examples of inert organic solvents are dimethoxyethane or acetone. The preferred alkali iodides are NaI, KI or LiI. The reaction usually proceeds with heating to below the boiling point of the organic solvent. The reaction progress can be traced by silica gel TLC and is terminated upon the disappearance of the above compound. The 2'-acetyl group and 4',4''-di-iodo group of the thus-obtained 2'-O-acetyl-4',4''-di-deoxy-4',4''-diiodo-desmycosin are removed, preferably prior to deiodization.

The de-4',4''-diiodization is effected by reacting 2'-O-acetyl-4',4''-dideoxy-4',4''-diiodo-desmycosin with tributyltin hydride and a catalytic amount of azobis-(isobutyronitrile) in an inert organic solvent. The preferred organic solvents are benzene or toluene. The reaction proceeds under an atmosphere of inert gas such as argon, and below the boiling point of the organic solvent. The reaction progress can be traced by silica gel TLC and is terminated upon the disappearance of 2'-O-acetyl-4',4''-dideoxy-4',4''-diiodo-desmycosin.

The de-2'-acetylation is performed with heating in methanol. The reaction progress can be traced by silica gel TLC, and is terminated upon the disappearance of 2'-O-acetyl-4',4''-dideoxy-desmycosin.

The deformylation is conducted with reflux of the inert organic solvent. The preferred inert organic solvent is benzene. The reaction progress can be checked by silica gel TLC and is terminated upon observing 4',4''-dideoxy-desmycosin.

Isolation of the intermediate in the production of the compound [1c] can be performed by pouring the reaction mixture into water, adjusting to approximately pH 9 with an alkali such as aqueous ammonia, extracting with a water-immiscible organic solvent such as chloroform, washing and concentrating. Further purification is effected by column chromatography using silica gel, active alumina or an adsorption resin.

The product [1c] can also be purified, if required, by column chromatography.

The minimum inhibitory concentration of compound [1] of the present invention is shown in Table 1.

The following examples illustrate the present invention:

In the examples, the Rf values are measured, if not specified, by TLC using the following carrier and developers:

Carrier: Merck, DC-Fertigplatten Kiesel Gel 60F$_{254}$, Art 5715.

Developer:
a: chloroform-methanol-aqueous ammonia (150:10:1)
b: chloroform-methanol-acetic acid-water (80:7:7:1)
c: benzene-acetone (4:1)
d: benzene-acetone (8:1)
e: hexane-benzene-acetone-ethyl acetate-methanol (90:80:25:60:30)

TABLE 1

| MIC (mcg/ml) | | | Control | | |
|---|---|---|---|---|---|
| Samples | Compound [1] | | desco- | erythro- | josa- |
| Test organisms | $R_1 = H$ | $R_1 = OH$ | mycin | mycin | mycin |
| *Staphylococcus aureus* ATCC 6538P | ≦0.05 | 0.1 | 0.8 | ≦0.05 | 0.4 |
| *Staphylococcus aureus* MS353 | ≦0.05 | ≦0.05 | 0.8 | 0.1 | 0.8 |
| *Staphylococcus aureus* MS353AO* | 0.8 | 25 | >100 | >100 | >100 |
| *Staphylococcus aureus* 0116* | 0.8 | 3.1 | 3.1 | >100 | >100 |
| *Staphylococcus aureus* 0119* | >100 | 12.5 | >100 | >100 | >100 |
| *Staphylococcus aureus* 0127* | >100 | 6.3 | >100 | >100 | >100 |
| *Streptococcus pyogenes* N.Y.5 | ≦0.05 | ≦0.05 | ≦0.05 | ≦0.05 | ≦0.05 |
| *Streptococcus pyogenes* 1022 | >100 | 25 | >100 | >100 | >100 |

*Macrolide antibiotics-resistant A group strain (clinical isolates of erythromycin-, oleandomycin- and 16-member-ring-macrolide-resistant strain)

EXAMPLE 1

19-deformyl-4'-deoxy-desmycosin:

[(C$_6$H$_5$)$_3$P]$_3$RhCl (3.9 g) was added to 4'-deoxy-desmycosin (3 g) dissolved in dry benzene (73 ml) and the mixture was reacted at 80° C. for six hours. The benzene was distilled off in vacuo, a small amount of acetone was added to the residue, and the precipitate was filtered. The filtered solution was concentrated in vacuo, and the residue was dissolved in benzene (20 ml) and extracted three times with 0.2 N HCl (40 ml). The aqueous layer was adjusted to pH 9 by dil. aqueous ammonia and extracted three times with chloroform (40 ml). The chloroform layer was dried by adding anhydrous magnesium sulfate, and dried in vacuo to obtain 19-deformyl-4'-deoxy-desmycosin (2 g).

TLC: Rfa=0.53, Rfb–0.25

Mass (CI) m/e: 728 (MH$^+$), 710, 379, 363, 176, 158.

NMR (100 MHz-CDCl$_3$) δppm: 1.77 (s., 3H), 2.28 (s., 6H), 3.48 (s., 3H), 3.61 (s., 3H), 4.24 (d., 1H), 4.55 (d., 1H), 4.94 (1H), 5.85 (d., 1H), 6.29 (d., 1H), 7.28 (d., 1H).

EXAMPLE 2

4'-deoxy-desmycosin:

(1) 2',4''-di-O-acetyl-desmycosin:

Acetic anhydride (25 ml) was added to tylosin (60 g) dissolved in acetone (300 ml), and the mixture was stirred at room temperature for 1.5 hours. The reaction mixture was poured into ice water (3 lit.), adjusted to pH 9 by adding aqueous ammonia and the precipitated 2'-O-acetyl-tylosin was filtered and then dissolved in 0.4 N HCl (50 ml) and the mixture was stirred at room temperature for one hour. The reaction mixture was adjusted to pH 9 by adding aqueous ammonia and extracted with chloroform (500 ml). The chloroform layer was washed with water, dried by adding anhydrous magnesium sulfate, and dried in vacuo to obtain a crude powder of 2'-O-acetyl-desmycosin (53 g), which was dissolved in dry dichloroethane (250 ml), to which was added pyridine (13 ml) and acetyl chloride (9.3 ml); and then the mixture was stirred at room temperature for one hour. The reaction mixture was poured into ice water (2.5 lit.), adjusted to pH 9 by ammonia, and extracted with chloroform (250 ml). The chloroform layer was washed with water, dried by adding anhydrous magnesium sulfate, concentrated in vacuo, and then the residue was purified by silica gel (1.5 kg) column chromatography using benzene-acetone (5:1). The fractions showing Rfe=0.42 were collected and dried in vacuo to obtain 2',4'-di-O-acetyl-desmycosin as a white powder (15.2 g).

TLC: Rfc=0.07, Rfd=0.01, Rfe=0.42

Mass (CI): 856 (MH+), 838, 622, 390, 235, 218, 217.

NMR (100 MHz, CdCl₃) δppm: 1.79 (s., 3H), 2.07 (s., 3H), 2.11 (s., 3H), 2.40 (s., 6H), 3.48 (S., 3H), 3.52 (s., 3H), 4.32 (d., 1H), 4.45 (d.d., 1H), 4.63 (d., 1H), 4.8-5.2 (2H), 5.90 (d., 1H), 6.29 (d., 1H), 7.32 (d., 1H), 9.68 (s., 1H).

(2) 2',4''-di-O-acetyl-4'-O-trifluoromethanesulfonyl-desmycosin:

Triethylamine (1 ml), dimethylaminopyridine (83 mg) and CF₃SO₂Cl (0.72 ml) were added to 2',4''-di-O-acetyl-desmycosin (2.32 g, 2.71 mM) dissolved in dry pyridine (9 ml), and the mixture was stirred at 0° C. for two hours. The reaction mixture was poured into ice water (300 ml), adjusted to pH 9 and the precipitate was filtered. The precipitate was dissolved in chloroform (100 ml), washed with 0.1 N HCl, water and dilute aqueous ammonia, and dried in vacuo to obtain a crude powder of 2',4''-di-O-acetyl-4'-O-trifluoromethanesulfonyl-desmycosin (2.6 g).

TLC: Rfc=0.53, Rfd=0.17, Rfe=0.78.

Elementary analysis [C₄₄H₆₈O₁₈NSF₃]:

|  | C % | H % | N % | S % | F % |
| --- | --- | --- | --- | --- | --- |
| Found: | 53.49 | 6.94 | 1.42 | 5.77 | 3.24 |
| Calculated: | 53.77 | 7.15 | 1.16 | 5.26 | 3.13 |

NMR (100 MHz, CDCl₃) δppm: 1.80 (s., 3H), 2.10 (s., 3H), 2.11 (s., 3H), 2.43 (s., 6H), 3.48 (s., 3H), 3.54 (s., 3H), 4.36 (d., 1H), 4.45 (d.d., 1H), 4.63 (d., 1H), 4.8-5.2 (3H), 5.90 (d., 1H), 6.29 (d., 1H), 7.32 (d., 1H), 9.67 (s., 1H).

(3) 2',4''-di-O-acetyl-4'-deoxy-4'-iodo-desmycosin:

NaI (1.52 g) was added to 2',4''-di-O-acetyl-4'-O-trifluoromethanesulfonyl-desmycosin (2.0 g) dissolved in hexamethylphosphorotriamide (8 ml), and the mixture was reacted at 70° C. for 40 hours. The reaction mixture was poured into ice water (200 ml), adjusted to pH 9 by adding dilute aqueous ammonia and the precipitate was collected by filtration. The filtrate was dissolved in chloroform (50 ml), washed with water, dried with anhydrous magnesium sulfate and concentrated in vacuo. The residue was purified by silica gel (70 g) column chromatography using benzene-acetone (9:1). The fractions showing Rfc=0.59 were collected and concentrated in vacuo to obtain 2',4''-di-O-acetyl-4'-iodo-desmycosin (260 mg).

TLC: Rfc=0.59, Rfd=0.22, Rfe=0.80.

Beilstein reaction: positive.

Mass (CI): 966 (MH+), 948, 650, 623, 605, 407, 389, 371, 344, 326, 217, 198.

(4) 2'-O-acetyl-4'-deoxy-4'-iodo-desmycosin:

2',4''-di-O-acetyl-4-deoxy-4'-iodo-desmycosin (130 mg) was added to a 0.15% NaOCH₃—methanol solution (1.5 ml) and the mixture was stirred at room temperature for one hour. The reaction was stopped by adding water (20 ml) and the mixture was extracted with chloroform (20 ml). The chloroform layer was washed with water, dried with anhydrous magnesium sulfate and dried in vacuo to obtain 2'-O-acetyl-4'-deoxy-4'-iodo-desmycosin (110 mg).

TLC: Rfc=0.27, Rfd=0.07, Rfe=0.61.

(5) 4'-deoxy-desmycosin:

Catalytic amounts of azobisisobutyronitrile and tributyltin hydride (37.8 μl) were added to 2'-O-acetyl-4'deoxy-4'-iodo-desmycosin dissolved in dry benzene (2.2 ml), and the mixture was reacted at 60° C. for three hours under an atmosphere of argon. Chloroform (20 ml) was added to the reaction mixture, which was then washed with dilute aqueous ammonia, dried with anhydrous magnesium sulfate and concentrated in vacuo. The residue was purified by silica gel (5 g) column chromatography using benzene-acetone (2:1). The fractions showing Rfe=0.17 were collected and concentrated in vacuo. Methanol (10 ml) was added to the residue and the mixture was refluxed for 16 hours. The reaction mixture was dried in vacuo to obtain 4'-deoxy-desmycosin (37 mg).

TLC: Rfa=0.38, Rfb=0.15.

Mass (CI): 756 (MH+), 738, 582, 564, 547, 407, 391, 389, 175, 174, 158.

NMR (100 MHz, CDCl₃) δppm: 1.77 (s., 3H), 2.26 (s., 6H), 3.49 (s., 3H), 3.61 (s., 3H), 4.20 (d., 1H), 4.56 (d., 1H), 4.98 (1H), 5.92 (d., 1H), 6.28 (d., 1H), 7.34 (d., 1H), 9.70 (s., 1H).

EXAMPLE 3

19-deformyl-4''-deoxy-desmycosin:

[(C₆H₅)₃P]₃RhCl (4.6 g) was added to 4''-deoxy-desmycosin (3.5 g) dissolved in dry benzene (85 ml), and the mixture was reacted at 80° C. for six hours. The benzene was distilled off in vacuo. A small amount of acetone was added to the residue and the precipitate was filtered. The filtrate was concentrated in vacuo. The residue dissolved in benzene (20 ml) was extracted three times with 0.2 N HCl (40 ml). The aqueous layer was adjusted to pH 9 by adding dilute aqueous ammonia and extracted three times with chloroform (40 ml). The chloroform layer was dried with anhydrous magnesium sulfate, and then dried in vacuo to yield 19-deformyl-4''-deoxy-desmycosin (2.3 g).

TLC: Rfa=0.44, Rfb=0.27.

Mass (CI) m/e: 728 (MH+), 710, 553, 190, 174, 159, 127.

NMR (100 MHz-CDCl₃) δppm: 1.78 (s., 3H), 2.50 (s., 6H), 3.40 (s., 3H), 3.48 (s., 3H), 4.29 (d., 1H), 4.64 (d., 1H), 5.00 (1H), 5.85 (d., 1H), 6.24 (d., 1H), 7.25 (d., 1H).

EXAMPLE 4

(1) 2',4'-di-O-acetyl-desmycosin:

Acetic anhydride (3.0 ml) was added to desmycosin (5.0 g. 6.48 mM) dissolved in dry dichloroethane (25 ml), and the mixture was stirred at room temperature for one hour. The reaction mixture was shaken while adding dilute aqueous ammonia until the mixture reached pH 9. The dichloroethane layer was dried with anhydrous magnesium sulfate and dried in vacuo to obtain 2',4'-di-O-acetyl-desmycosin (4.6 g).

TLC: Rfc=0.14, Rfd=0.04, Rfe=0.48.

Mass (CI): 856 (MH+), 838, 666, 664, 407, 391, 276, 258, 216, 175.

NMR (100 MHz, CDCl₃) δppm: 1.79 (s., 3H), 2.04 (s., 3H), 2.05 (s., 3H), 2.34 (s., 6H), 3.49 (s., 3H), 3.61 (s., 3H), 4.31 (d., 1H), 4.56 (d., 1H), 4.73 (d.d., 1H), 4.88 (d.d., 1H), 5.00 (1H), 5.91 (d., 1H), 6.29 (d., 1H), 7.33 (d., 1H), 9.67 (s., 1H).

(2) 2',4'-di-O-acetyl-4''-O-trifluoromethanesulfonyl-desmycosin:

Pyridine (1.08 ml) and $(CF_3SO_2)_2O$ (1.81 ml) were added to 2',4'-di-O-acetyl-desmycosin (4.6 g) dissolved in dichloroethane (25 ml), and the mixture was stirred at 0° C. for one hour. The reaction mixture was poured into ice water (100 ml) and extracted with chloroform. The chloroform layer was washed with water and dilute aqueous ammonia, in this order, dried with anhydrous magnesium sulfate, and dried in vacuo to yield a crude powder of 2',4'-di-O-acetyl-4''-O-trifluoromethanesulfonyl-desmycosin (4.6 g).

TLC: Rfc=0.41

Elementary analysis $[C_{44}H_{68}NO_{18}SF_3]$:

|  | C % | H % | N % | S % | F % |
|---|---|---|---|---|---|
| Found: | 53.49 | 6.94 | 1.42 | 5.77 | 3.24 |
| Calculated: | 53.43 | 7.13 | 1.14 | 5.22 | 3.40 |

NMR (100 MHz, CDCl$_3$) δppm: 1.79 (s., 3H), 2.06 (s., 6H), 2.38 (s., 6H), 3.51 (s., 3H), 3.60 (s., 3H), 4.32 (d., 1H), 4.41 (1H), 4.63 (d., 1H), 4.75 (d.d., 1H), 4.89 (d.d., 1H), 5.00 (1H), 5.91 (d., 1H), 6.30 (d., 1H), 7.32 (d., 1H), 9.67 (s., 1H).

(3) 2',4'-di-O-acetyl-4''-deoxy-4''-iodo-desmycosin:

NaI (1.67 g) was added to 2',4'-di-O-acetyl-4''-O-trifluoromethanesulfonyl-desmycosin (2.2 g) dissolved in dry dimethoxyethane (11 ml), and the mixture was reacted at 70° C. for six hours. The reaction mixture was poured into water (100 ml) and extracted with chloroform. The chloroform layer was washed with dilute aqueous ammonia and water in this order, dried with anhydrous magnesium sulfate and concentrated in vacuo. The residue was dissolved in a small amount of benzene and purified by silica gel (75 g) column chromatography using benzene-acetone (10:1). The fractions showing Rfc=0.43 were collected and dried in vacuo to yield 2',4'-di-O-acetyl-4''-deoxy-4''-iodo-desmycosin (339 mg).

TLC: Rfc=0.43, Rfd=0.15, Rfe=0.74

Beilstein reaction: positive

Mass (CI): 966 (MH+), 948, 840, 832, 710, 692, 682, 664, 409, 407, 391, 389, 373, 371, 285, 286, 274, 258.

(4) 2',4'-di-O-acetyl-4''-deoxy-desmycosin:

Catalytic amounts of azobisisobutyronitrile and tributyltin hydride (33 μl) were added to 2',4'-di-O-acetyl-4''-deoxy-4''-iodo-desmycosin (100 mg, 0.104 mM) dissolved in dry benzene (2 ml), and the mixture was reacted at 60° C. for three hours under an atmosphere of argon. Water (20 ml) was added to the reaction mixture which was then extracted with chloroform (20 ml). The chloroform layer was dried with anhydrous magnesium sulfate and concentrated in vacuo. The residue was purified by silica gel (5 g) column chromatography using benzene-acetone (6:1). The fractions showing Rfc=0.22 were collected and dried in vacuo to yield 2',4'-di-O-acetyl-4''-deoxy-desmycosin.

TLC: Rfc=0.22, Rfd=0.05, Rfe=0.59.

Mass (CI): 840 (MH+), 822, 276, 258, 159, 127.

(5) 4''-deoxy-desmycosin:

Methanol (10 ml) was added to 2',4'-di-O-acetyl-4''-deoxy-desmycosin obtained hereinabove and the mixture was refluxed for 16 hours. The reaction mixture was dried in vacuo to obtain 4''-deoxy-desmycosin (41 mg).

TLC: Rfa=0.29, Rfb-0.18

Mass (CI): 756 (MH+), 738, 597, 581, 563, 407, 391, 389, 192, 174, 159, 127.

NMR (100 MHz, CDCl$_3$) δppm: 1.80 (s., 3H), 2.50 (s., 6H), 3.40 (s., 3H), 3.49 (s., 3H), 4.25 (d., 1H), 4.64 (d., 1H), 5.02 (1H), 5.93 (d., 1H), 6.25 (d., 1H), 7.32 (d., 1H), 9.69 (s., 1H).

EXAMPLE 5

19-deformyl-4''-deoxy-desmycosin:

(1) 2',4'-di-O-acetyl-19-deformyl-desmycosin:

Acetic anhydride (2.5 ml) was added to 19-deformyl-desmycosin (3.9 g) [Jap. Pat. Unexam. Publ. No. 556-55399] dissolved in dry dichloroethane (20 ml), and the mixture was stirred at room temperature for one hour. The reaction mixture was shaken while adding dilute aqueous ammonia until the mixture reached pH 9. The dichloroethane layer was dried with anhydrous magnesium sulfate and dried in vacuo to obtain 2',4'-di-O-acetyl-19-deformyl-desmycosin (4.15 g).

TLC: Rfc=0.26

Mass (CI) m/e: 828 (MH+), 810, 379, 276, 258, 175, 129.

(2) 2',4'-di-O-acetyl-19-deformyl-4''-O-trifluoromethanesulfonyl-desmycosin:

$(CF_3SO_2)_2O$ (0.17 ml) was added at 0° C. to 2',4'-di-O-acetyl-19-deformyl-desmycosin (4.15 g) dissolved in dry pyridine (16 ml) and the mixture was stirred at 0° C. for one hour. The reaction mixture was poured into ice water (100 ml) and extracted with chloroform. The chloroform layer was washed with water, dilute HCl and dilute aqueous ammonia, in this order, dried with anhydrous magnesium sulfate and dried in vacuo to yield a crude powder of 2',4'-di-O-acetyl-19-deformyl-4''-O-trifluoromethanesulfonyl-desmycosin (4.45 g).

TLC: Rfc=0.59

Elementary analysis $[C_{43}H_{68}NO_{17}SF_3]$:

|  | C % | H % | N % | S % | F % |
|---|---|---|---|---|---|
| Found: | 53.91 | 7.29 | 1.28 | 5.50 | 3.58 |
| Calculated: | 53.80 | 7.14 | 1.46 | 5.94 | 3.34 |

(3) 2',4'-di-O-acetyl-19-deformyl-4''-deoxy-4''-iodo-desmycosin:

NaI (3.0 g) was added to 2',4'-di-O-acetyl-19-deformyl-4''-O-trifluoromethanesulfonyl-desmycosin (4.0 g) dissolved in dry dimethoxyethane (20 ml), and the mixture was reacted at 70° C. for 2.5 hours. The reaction mixture was poured into water (200 ml) and extracted with chloroform. The chloroform layer was washed with dilute aqueous ammonia and water, dried with anhydrous magnesium sulfate and concentrated in vacuo. The residue was dissolved in a small amount of benzene and purified by silica gel (150 g) column chromatography using benzene-acetone (16:1). The fractions showing Rfc=0.62 were collected and dried in vacuo to obtain 2',4'-di-O-acetyl-19-deformyl-4''-deoxy-4''-iodo-desmycosin (559 mg).

TLC: Rfc=0.62

Mass (CI) m/e: 938 (MH+), 920, 870, 812, 682, 654, 636, 379, 363, 345, 285, 276, 258.

(4) 2',4'-di-O-acetyl-19-deformyl-4''-deoxy-desmycosin:

Catalytic amounts of azobisisobutyronitrile and tributyltin hydride (188 μl) were added to 2',4'-di-O-acetyl- 19-deformyl-4"-deoxy-4"-iodo-desmycosin (555 mg) dissolved in dry benzene (11 ml), and the mixture was reacted at 60° C. for three hours under an atmosphere of argon. Water (50 ml) was added to the reaction mixture which was then extracted with chloroform (25 ml). The chloroform layer was dried with anhydrous magnesium sulfate and concentrated in vacuo. The residue was purified by silica gel (20 g) column chromatography using benzene-acetone (9:1). The fractions showing RFc=0.40 were collected and dried in vacuo to yield 2',4'-di-O-acetyl-19-deformyl-4"-deoxy-desmycosin (490 mg).

(5) 19-deformyl-4"-deoxy-desmycosin:

Methanol (20 ml) was added to 2',4'-di-O-acetyl-19-deformyl-4"-deoxy-desmycosin (490 mg) and the mixture was refluxed for 16 hours. The reaction mixture was dried in vacuo to yield 19-deformyl-4"-deoxy-desmycosin (450 mg).

TLC: Rfa=0.44, Rfb-0.27

Mass (CI) m/e: 728 (MH+), 710, 553, 190, 174, 159, 127.

EXAMPLE 6

4',4"-di-deoxy-19-deformyl-desmycosin:

(1) 2'-O-acetyl-4',4"-di-deoxy-4',4"-diiodo-desmycosin:

Pyridine (0.59 ml) and $CF_3SO_2Cl$ (0.99 ml) were added at 0° C. to 2'-O-acetyl-4'-deoxy-4'-iodo-desmycosin (2.72 g), obtained in Example 2 (4) hereinbefore, dissolved in dry dichloroethane (14 ml), and the mixture was stirred at 0° C. for one hour. The reaction mixture was poured into ice water (60 ml) and extracted with chloroform. The chloroform layer was washed with water and dilute aqueous ammonia, dried with anhydrous magnesium sulfate and dried in vacuo to obtain 2'-O-acetyl-4'-deoxy-4'-iodo-4"-O-trifluoromethanesulfonyl-desmycosin, which was dissolved in dry dimethoxyethane (10 ml). NaI (2.2 g) was added thereto and the mixture was reacted at 60° C. for four hours. The reaction mixture was poured into ice water (100 ml), and was adjusted to pH 9 by adding dilute aqueous ammonia and extracted with chloroform. The chloroform layer was washed with water, dried with anhydrous magnesium sulfate, concentrated in vacuo and purified by silica gel (150 g) column chromatography using benzene-acetone (20:1). The fractions showing Rfc=0.80 were collected and dried in vacuo to yield 2'-O-acetyl-4',4"-di-deoxy-4',4"-diiodo-desmycosin (439 mg).

TLC: Rfc=0.80, Rfd=0.50, Rfe=0.88.

(2) 4',4"-di-deoxy-desmycosin:

Catalytic amounts of azobisisobutyronitrile and tributyltin hydride (0.32 ml) were added to 2'-O-acetyl-4',4"-di-deoxy-4',4"-diiodo-desmycosin dissolved in dry benzene (10 ml), and the mixture was reacted at 60° C. under an atmosphere of argon. Water (100 ml) was added to the reaction mixture which was then extracted with chloroform (100 ml). The chloroform layer was dried with anhydrous magnesium sulfate and concentrated in vacuo. The residue was purified by silica gel (20 g) column chromatography using benzene-acetone (3:1). The fractions showing Rfe=0.24 were collected and dried in vacuo to yield 2'-O-acetyl-4',4"-di-deoxy-desmycosin. Methanol (40 ml) was added thereto and the mixture was refluxed for 16 hours. The reaction mixture was dried in vacuo to yield 4',4"-di-deoxy-desmycosin (198 mg).

TLC: Rfa=0.49, Rfb=0.19

Mass (CI): 740 (MH+), 722, 608, 606, 582, 565, 407, 391, 373, 175, 174, 159, 158, 127.

NMR (100 MHz, $CDCl_3$) δppm: 1.78 (s, 3H), 2.26 (s., 6H), 3.40 (s., 3H), 3.48 (s., 3H), 4.20 (d., 1H), 4.64 (d., 1H), 5.00 (1H), 5.95 (d., 1H), 6.28 (d., 1H), 7.33 (d., 1H), 9.70 (s., 1H).

(3) 4',4"-di-deoxy-19-deformyl-desmycosin:

$[(C_6H_5)_3P]_3RhCl$ (136 mg) was added to 4',4"-di-deoxy-desmycosin (100 mg) dissolved in dry benzene (2.5 ml), and the mixture was stirred at 80° C. for five hours. The reaction mixture was concentrated in vacuo. The residue was charged on a silica gel TLC plate (Merck A. G., Art 5717), which was developed with chloroform-methanol-conc. aqueous ammonia (150:10:1) and a band at Rf=0.60 was scraped.

The scraped silica gel was extracted with chloroform-methanol (1:1) and the extract was dried in vacuo to yield 4',4"-di-deoxy-19-deformyl-desmycosin (78 mg).

TLC: Rfa=0.60

NMR (100 MHz, $CDCl_3$) δppm: 1.78 (s., 3H), 2.27 (s., 6H), 3.40 (s., 3H), 3.48 (s., 3H), 4.24 (d., 1H, 7.3 Hz), 4.64 (d., 1H, 7.9 Hz), 4.98 (m., 1H), 5.89 (d., 1H, 10.3 Hz), 6.29 (d., 1H, 15.7 Hz), 7.29 (d., 1H, 15.7 Hz), Mass (CI, isobutane): 712 (MH+), 694, 363, 159, 158, 127.

What is claimed is:

1. A compound of the formula

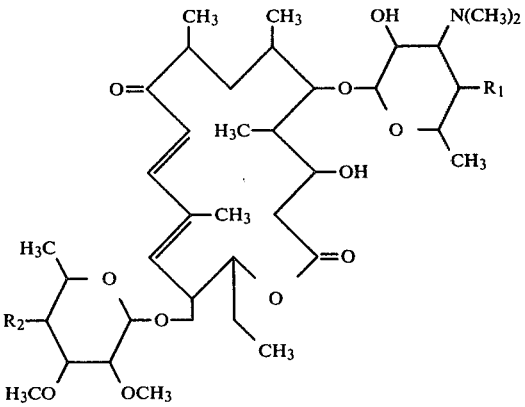

wherein $R_1$ and $R_2$ are hydrogen or hydroxyl and at least one of $R_1$ and $R_2$ is hydrogen, or a pharmaceutically acceptable salt thereof.

2. 19-deformyl-4'-deoxy-desmycosin or a pharmaceutically acceptable salt thereof.

3. 19-deformyl-4"-deoxy-desmycosin or a pharmaceutically acceptable salt thereof.

4. 4',4"-deoxy-19-deformyl-desmycosin or a pharmaceutically acceptable salt thereof.

* * * * *